(12) United States Patent
Kalb et al.

(10) Patent No.: US 10,327,659 B2
(45) Date of Patent: Jun. 25, 2019

(54) QUANTIZATION NOISE CANCELLATION IN A FEEDBACK LOOP

(71) Applicant: Analog Devices, Inc., Norwood, MA (US)

(72) Inventors: Arthur J. Kalb, Santa Clara, CA (US); Yogesh Jayaraman Sharma, Santa Clara, CA (US); Marvin Liu Shu, Daly City, CA (US)

(73) Assignee: Analog Devices, Inc., Norwood, MA (US)

( * ) Notice: Subject to any disclaimer, the term of this patent is extended or adjusted under 35 U.S.C. 154(b) by 150 days.

(21) Appl. No.: 15/621,621

(22) Filed: Jun. 13, 2017

(65) Prior Publication Data
US 2018/0132750 A1    May 17, 2018

Related U.S. Application Data

(60) Provisional application No. 62/492,406, filed on May 1, 2017, provisional application No. 62/421,650, filed
(Continued)

(51) Int. Cl.
| | |
|---|---|
| *A61B 5/00* | (2006.01) |
| *A61B 5/0428* | (2006.01) |
| *A61B 5/0452* | (2006.01) |
| *H03M 3/00* | (2006.01) |
| H03M 1/06 | (2006.01) |
| H03M 1/18 | (2006.01) |
| H03M 1/68 | (2006.01) |

(52) U.S. Cl.
CPC ........ *A61B 5/04288* (2013.01); *A61B 5/0006* (2013.01); *A61B 5/0452* (2013.01); *H03M 3/414* (2013.01); H03M 1/0673 (2013.01); H03M 1/18 (2013.01); H03M 1/68 (2013.01); H03M 3/46 (2013.01)

(58) Field of Classification Search
CPC . A61B 5/04288; A61B 5/0452; A61B 5/0006; H03M 3/414
USPC .................................................. 341/155, 120
See application file for complete search history.

(56) References Cited

U.S. PATENT DOCUMENTS

| | | |
|---|---|---|
| 5,327,133 A | 7/1994 | Greene |
| 5,635,864 A | 6/1997 | Jones |

(Continued)

FOREIGN PATENT DOCUMENTS

DE        102010036793        4/2014

OTHER PUBLICATIONS

"U.S. Appl. No. 15/334,011, Preliminary Amendment Filed, Jan. 11, 2018", 8 pgs.
"U.S. Appl. No. 15/334,011, Non Final Office Action dated Feb. 21, 2018", 4 pgs.
"German Application Serial No. 202017106869.2, German Search Report dated Aug. 9, 2018", 7 pgs.

(Continued)

*Primary Examiner* — Brian K Young
(74) *Attorney, Agent, or Firm* — Schwegman Lundberg & Woessner, P.A.

(57) ABSTRACT

An analog front end (AFE) system for substantially eliminating quantization error or noise can combine an input of an integrator circuit in the AFE system with an input of the digital-to-analog converter (DAC) circuit in the feedback loop of the AFE system. By combining the input of the integrator with the input of the DAC circuit in the feedback loop, the in-band quantization noise of the filter can be substantially eliminated, thereby improving measurement accuracy.

24 Claims, 6 Drawing Sheets

Related U.S. Application Data on Nov. 14, 2016, provisional application No. 62/421,344, filed on Nov. 13, 2016.

(56) References Cited

U.S. PATENT DOCUMENTS

| | | | |
|---|---|---|---|
| 6,271,782 B1 | 8/2001 | Steensgaard-Madsen | |
| 7,095,345 B2 | 8/2006 | Nguyen et al. | |
| 7,385,443 B1 | 6/2008 | Denison | |
| 7,423,567 B2 | 9/2008 | Melanson | |
| 8,094,051 B2 | 1/2012 | Bos | |
| 8,265,769 B2 | 9/2012 | Denison | |
| 8,836,566 B2 * | 9/2014 | Kabir | H03M 1/002 |
| | | | 341/158 |
| 9,214,950 B1 * | 12/2015 | Davis | H03M 1/0621 |
| 9,391,628 B1 | 7/2016 | Lyden et al. | |
| 9,419,642 B1 | 8/2016 | Nguyen | |
| 9,455,737 B1 * | 9/2016 | Rajaee | H03M 3/464 |
| 9,588,497 B1 | 3/2017 | Monk et al. | |
| 10,135,459 B2 | 11/2018 | Sharma et al. | |
| 2007/0126615 A1 | 6/2007 | Kim et al. | |
| 2009/0079606 A1 | 3/2009 | Terry | |
| 2009/0085785 A1 | 4/2009 | Gerfers et al. | |
| 2010/0066577 A1 | 3/2010 | Huang | |
| 2010/0075624 A1 | 3/2010 | Shanan | |
| 2012/0038500 A1 | 2/2012 | Dijkmans et al. | |
| 2012/0154193 A1 | 6/2012 | Chang et al. | |
| 2012/0281786 A1 | 11/2012 | Lindemann et al. | |
| 2015/0145571 A1 | 5/2015 | Perrott | |
| 2015/0256194 A1 | 9/2015 | Saito | |
| 2017/0230019 A1 | 8/2017 | Chandrakumar et al. | |
| 2018/0115320 A1 | 4/2018 | Sharma et al. | |
| 2018/0138920 A1 | 5/2018 | Sharma et al. | |

OTHER PUBLICATIONS

"U.S. Appl. No. 15/334,011, Notice of Allowance dated Oct. 17, 2017", 8 pgs.

"U.S. Appl. No. 15/334,011, Non Final Office Action dated Feb. 10, 2017", 6 pgs.

"Optimum Selection of Capacitive Array for Multibit Sigma-Delta Modulators without DEM", (Jan. 1, 2009), 4 pgs.

Bohorquez, Jose L., et al., "A Digitally-Assisted Sensor Interface for Biomedical Applications", 2010 Symposium on VLS! Circuits / Technical Digest of Technical Papers, (2010), 217-218.

Bryant, Michael D., et al., "A Mixed Signal (Analog-Digital) Integrator Design", IEEE Transactions on Circuits and Systems—1: Regular Papers, 59)7), (Jul. 2012), 14-9.

Denison, Tim, et al., "A 2uW 100 n V/rtHz Chopper-Stabilized Instrumentation Amplifier for Measurement of Neutral Field Potentials", IEEE Journal of Solid-State Circuits, vol. 42, No. 12, (Dec. 2007), 2934-2945.

Muller, Rikky, et al., "A 0.13 mm2, 5uW, DC-Coupled Neutral Signal Acquisition IC With 0.5 V Supply", IEEE Journal of Solid-State Circuits, vol. 47, No. 1, (Jan. 2012), 232-243.

"U.S. Appl. No. 15/334,011, Response filed Aug. 9, 2017 to Non Final Office Action dated Feb. 10, 2017", 11 pgs.

"U.S. Appl. No. 15/334,011, Examiner Interview Summary dated Aug. 8, 2017", 3 pgs.

"U.S. Appl. No. 15/334,011, Notice of Allowance dated Jul. 12, 2018", 7 pgs.

"U.S. Appl. No. 15/634,441, Notice of Allowance dated Jan. 17, 2019", 9 pgs.

"U.S. Appl. No. 15/334,011, Response filed May 21, 2018 to Non Final Office Action dated Feb. 21, 2018", 9 pgs.

* cited by examiner

QUANTIZATION NOISE CANCELLATION IN A FEEDBACK LOOP

CLAIM OF PRIORITY

This application claims the benefit of priority of U.S. Provisional Patent Application Ser. No. 62/421,344, titled "INTERFERENCE-IMMUNE DIAGNOSTIC QUALITY ECG RECORDING FOR WIRELESS PATIENT MONITORING APPLICATIONS" to Arthur J. Kalb et al., filed on Nov. 13, 2016, and U.S. Provisional Patent Application Ser. No. 62/421,650, titled "INTERFERENCE-IMMUNE DIAGNOSTIC QUALITY ECG RECORDING FOR WIRELESS PATIENT MONITORING APPLICATIONS" to Arthur J. Kalb et al., filed on Nov. 14, 2016, and U.S. Provisional Patent Application Ser. No. 62/492,406, titled "QUANTIZATION NOISE CANCELLATION IN A FEEDBACK LOOP" to Arthur J. Kalb et al., filed on May 1, 2017, the entire contents of each being incorporated herein by reference.

FIELD OF THE DISCLOSURE

This disclosure relates generally to integrated circuits, and more particularly but not by way of limitation, analog front ends and analog-to-digital converters.

BACKGROUND

In many electronics applications, an analog front end (AFE) can translate analog electrical signals representing real-world phenomenon, e.g. light, sound, temperature, or pressure, to a digital output signal to be used for digital processing, e.g. for further signal processing. For instance, in some precision measurement systems, electronics can be provided with one or more sensors to make measurements and generate analog signals. The analog signals can be provided to an analog-to-digital converter (ADC) to generate a digital representation for further processing.

AFEs can be found in many places such as broadband communication systems, audio systems, receiver systems, etc. AFEs can be used in a broad range of applications including communications, energy, healthcare, instrumentation and measurement, motor and power control, industrial automation and aerospace/defense.

SUMMARY OF THE DISCLOSURE

Analog front ends (AFEs) can be used for various applications, including wireless patient monitoring applications, for example. The present inventors recognize that when designing electrocardiogram (ECG) measurement front ends, one problem to be solved is minimizing power consumption while maintaining a fixed noise budget. The present inventors recognize that capacitive sampling at the input of an ADC, within an AFE, contributes significant thermal noise, commonly referred to as KT/C noise. This can be avoided by introducing a continuous-time signal gain before the ADC. Taking continuous-time signal gain before any sampling activity reduces the impact of sampling noise. However, the manner of taking this continuous-time signal gain in prior art can have several drawbacks and limitations, which can be overcome by various techniques described in this disclosure.

The first drawback is that continuous-time gains, implemented with an amplifier, have limited dynamic range at the output, thereby limiting the realizable gain. It is desirable to take as a large a gain as possible. The second drawback of continuous-time gains is that they often require the introduction of resistors. Resistors have an inherent thermal noise based on their resistance value; the voltage noise power is proportional to the value of the resistance. Furthermore, the introduction of resistors requires a continuous drive of currents to support the voltage across the resistor. This burns power and doing so typically requires amplifier architectures that burn even more power. When resistors are not used for the continuous-time gain, capacitors are generally used. The challenge then becomes establishing a suitable bias on the capacitors.

The present invention addresses the first of these drawbacks by subtracting a representation of the input signal before amplification. This allows for an extended dynamic range at the circuit input while not requiring an extended dynamic range at the output of the amplifier. As it is generally not practical to subtract a high-resolution representation, the present invention quantizes a filtered ADC output to provide as the representation of the input. The subtraction loop described above crosses from the digital domain of the ADC output back to the analog domain of the amplifier. This is achieved with a feedback digital-to-analog converter (DAC). The inventors have combined this DAC with the gain stage.

The second drawback is addressed by using capacitive gain elements both for the AFE input signal and the DAC feedback signal. In order to establish suitable biases on the capacitors, the AFE samples the input and DAC feedback signals. However, although sampling noise is present on the output, the output is provided in a manner that it can be periodically sampled such that the sampled noise is substantially rejected. This disclosure describes techniques to extend the concept to a capacitive DAC. This combined solution achieves the goals of increasing the realizable gain before the ADC, while doing this in a way that does not cause sampling noise to appear at the output.

The aforementioned quantization normally introduces an additional noise component known as quantization noise. The quantized filtered ADC output can be recombined with the ADC output to form the AFE output. The present invention utilizes the fact that both the input and the output of the quantization process are digital and known precisely. Thus it becomes possible to recombine them in such a way that the otherwise-dominant quantization noise is substantially rejected at the system output.

In some aspects, this disclosure is directed to an analog front end (AFE) system for compensating quantization error. The AFE system can comprise a gain circuit including a first input configured to receive an input signal, a second input configured to receive a feedback signal using a feedback path, and an output configured to provide an amplified version of the difference between the input signal and the feedback signal; an analog-to-digital converter (ADC) configured to receive a gain circuit output signal and output a digital output signal; a digital frequency-selective filter circuit configured to receive the ADC digital output signal and output a quantized filter circuit output signal; a digital-to-analog converter (DAC) circuit, the DAC circuit configured to receive the filter output signal and output the feedback signal to the second input of the gain circuit; and an AFE system output circuit configured to combine the ADC output signal and the filter circuit output signal, and output a quantization error-compensated AFE output signal.

In some aspects, this disclosure is directed to a method of analog-to-digital conversion that compensates for a quantization error component of the conversion.

The method can comprise receiving an analog input signal for conversion into a digital output signal; combining the analog input signal with a feedback signal to create difference signal; amplifying the difference signal; performing an analog-to-digital conversion on the amplified signal to create a converted digital signal; filtering the converted digital signal to generate a filtered signal with quantization error; performing a digital-to-analog conversion on the filtered signal to generate the said feedback signal; and combining the converted digital signal with the filtered signal to generate a system output in which the quantization error component is substantially reduced.

In some aspects, this disclosure is directed to an electrocardiogram (ECG) measurement circuit that can comprise an analog front end (AFE) system for compensating quantization error. The AFE system can include a gain circuit including a first input configured to receive an input signal and a second input configured to receive a feedback signal using a feedback path; an ADC circuit configured to receive a gain circuit output signal and output an ADC circuit output signal; a frequency-selective filter circuit configured to receive the ADC circuit output signal and output a filter circuit output signal; a quantizer circuit, the quantizer circuit configured to receive the filter circuit output signal and output a quantized signal; a digital-to-analog converter (DAC) circuit, the DAC circuit configured to receive the quantized signal and output the feedback signal to the second input of the gain circuit; and an AFE system output circuit configured to combine the ADC circuit output signal and the quantized signal and output a quantization error-compensated AFE output signal.

This overview is intended to provide an overview of subject matter of the present patent application. It is not intended to provide an exclusive or exhaustive explanation of the invention. The detailed description is included to provide further information about the present patent application.

Figure 1:
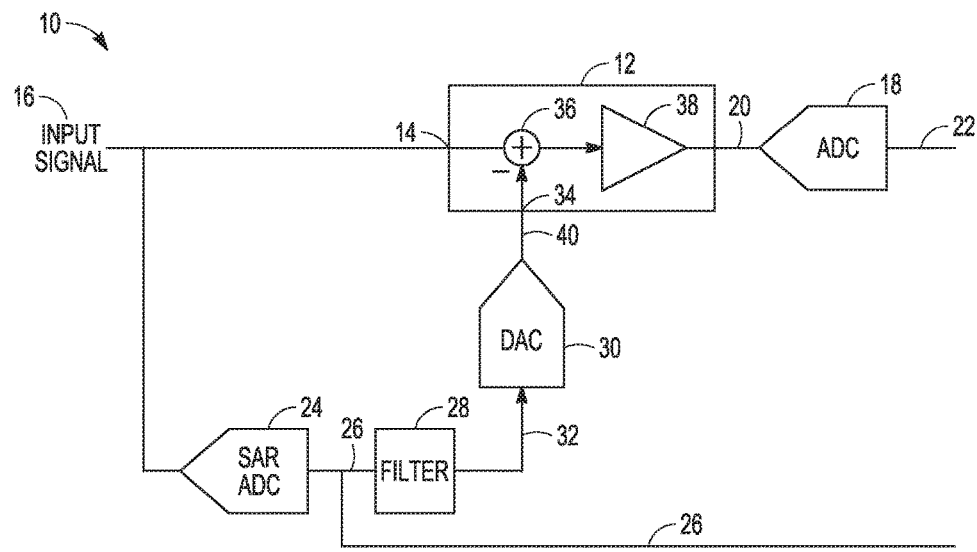
FIG. 1 depicts an example of a schematic diagram of an analog front end.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document describes, among other things, an analog front end (AFE) system capable of subtracting a quantized filtered representation of the input signal from the input and gaining the difference signal. The difference signal is then processed by an analog-to-digital converter (ADC) circuit. The filtered representation of the input signal is derived from the output of the analog-to-digital converter by filtering in the digital domain. A practical AFE system can quantize the filtered representation before being received as an input to the subtraction circuit. The subtraction circuit can employ a digital-to-analog converter (DAC) circuit to translate the quantized signal from the digital to the analog domain. A high resolution DAC can be difficult and/or costly to implement and so, in some example implementations, a lower resolution converter can be desirable; thus, quantizing the filtered representation can be desirable. The implication of quantizing the filtered representation is that the system acquires a quantization error, or noise, at the output of the ADC. The present invention substantially eliminates this quantization noise by recombining the ADC output with the quantized filtered representation of the input.

Another aspect of the invention is that the difference signal can be created using capacitive elements. Furthermore, the gained version of the difference signal can be periodically sampled in a manner that any sampled thermal noise, commonly known as KT/C noise, is substantially eliminated.

Another aspect of the invention is that the difference signal can be created using chopped capacitive-gain amplifiers (CGAs). This can be desirable due to their high common mode rejection ratio (CMRR), lack of resistive noise, and lack of noise folding. However, they can suffer from not having a convenient method for biasing. The basis for the CGA design in this front end can provide an advantage that a well-defined DC bias can be established. Although the CGA circuit can auto-zero, the input signal appears as a continuous-time signal to subsequent stages when sampled (provided complete settling occurs after each switch change). As such, there is immeasurable aliasing of the input and noise folding, while still passing the signal. The amplifier is designed such that the 1/f corner is lower than the chopping rate, allowing the signal to be up-modulated, amplified, and down-modulated without introducing noise or thermal noise folding.

Canceling the quantization noise and eliminating gain stage sampling noise can improve measurement accuracy. For example, the techniques of this disclosure can improve electrocardiogram (ECG) measurements. Among other things, this document describes a measurement channel capable of providing diagnostic quality ECG measurements, such as for battery-powered wireless patient monitoring. For example, each channel can provide 21-bit output at either 300 samples per second (SPS) or 600 SPS. The noise per channel can be approximately 1.5 microvolt (RMS) ($\mu V_{rms}$). For robust use in the face of severe interference, the input dynamic range can be greater than ±1 Volt (V), with an overload recovery time of less than 16.6 milliseconds (ms). Input bias currents can be maintained below 250 picoamperes (pA) such as not to interfere with other monitoring functions. The AFE architecture discussed suits itself to general analog-to-digital conversion and is not limited to ECG applications.

FIG. 1 depicts an example of a schematic diagram of an analog front end (AFE) system 10. The system 10 can include a gain circuit 12 having a first input 14 to receive an analog input signal 16, and an ADC circuit 18, e.g. a sigma-delta ADC, to receive an output 20 of the gain circuit 12. In the example configuration shown, the gain circuit 12 can include an adder circuit 36 and a gain circuit 38, e.g. a capacitive gain amplifier (CGA).

The ADC 18 can generate a first digital output signal 22 corresponding to the analog input signal 16, e.g. an ECG output signal. The system 10 can include a second ADC circuit 24, e.g. a successive approximation register (SAR) ADC circuit, to receive the analog input signal 16 and generate a first filter input signal 26. The filter input signal 26 may serve as an independent output, e.g. a pacemaker detection output, corresponding to the analog input signal 16. In the example configuration depicted in FIG. 1, the second ADC 24 can be coupled to a filter circuit 28, e.g. a low-pass filter circuit, such that an input of the filter 28 can receive the first filter input signal 26. An input of the digital-to-analog converter (DAC) circuit 30 can receive a filtered output 32 of the filter circuit 28 and generate an analog signal 40. As seen in FIG. 1, the analog signal 40 from the DAC circuit 30 can be applied to a second input 34 of the gain circuit 12. The adder circuit 36 can subtract the DAC analog output signal 40—from the original analog input signal 16. It should be noted that the adder circuit 36 is depicted for conceptual purposes but in some configurations forms a part of the gain circuit 12 itself.

In some examples, the subtraction and gain can be performed in a CGA, which can then be fed into a high resolution ADC 18, such as a sigma-delta converter, for linearity. An estimate for the low frequency content can be formed by sampling the analog input signal 16 with a low-accuracy successive approximation register (SAR) converter 24 and then low-pass filtering with filter 28.

The low-pass filtered output can be quantized and provided as in input to the DAC 30. A SAR converter can be well suited to the low resolution accuracy, yielding an excellent conversion efficiency. Also, implementing the low-pass filter 28 in the digital domain can allow for the realization of long time constants without a large capacitor. A drawback of this architecture can be slow overload recovery due to the low-pass filter 28. Resetting the filter 28 can result in undesirable measurement artifacts. Reducing the time constant of the filter 28 can subtract signal and result in an undesirable high-pass corner to the output signal 22, e.g. an ECG output. Another issue that can arise is that the quantization steps of the SAR ADC 24 and DAC 30 path can be introduced as artifacts into the output signal.

Figure 2:
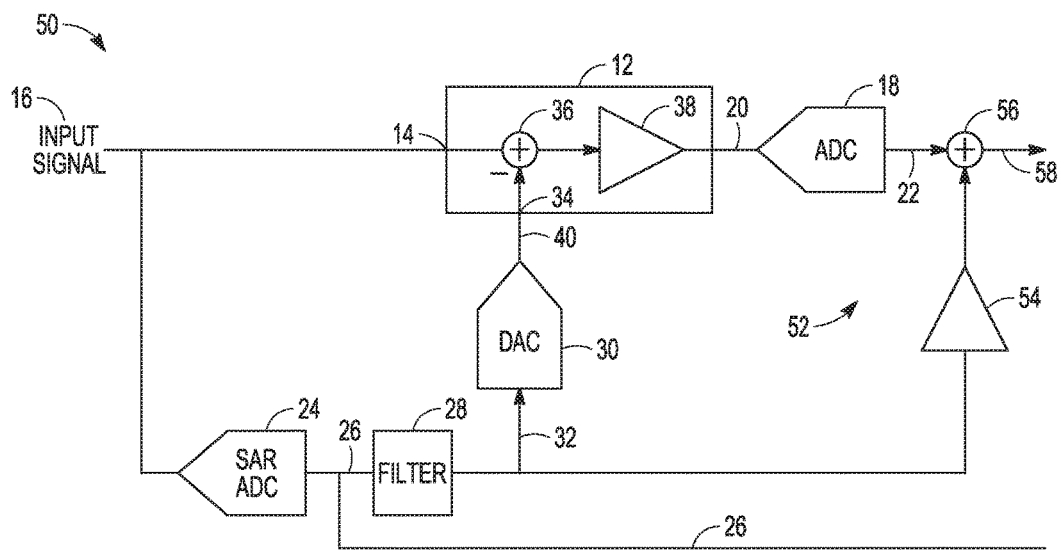
FIG. 2 depicts another example of a schematic diagram of an analog front end.

FIG. 2 depicts another example of a schematic diagram of an analog front end system 50. The system 50 in FIG. 2 can include many of the same components as the system 10 in FIG. 1. For purposes of conciseness, similar components will not be described again. The system 50 in FIG. 2 can include a recombination path 52. For example, the recombination path 52 can include a scaling circuit 54 and an adder circuit 56. The adder circuit 56 can combine a scaled version of the filtered output, e.g., the filtered output 32 of the filter circuit 28, with the first digital output signal 22 from the ADC 18 to generate an output signal 58, e.g. an ECG output signal.

Figure 3:
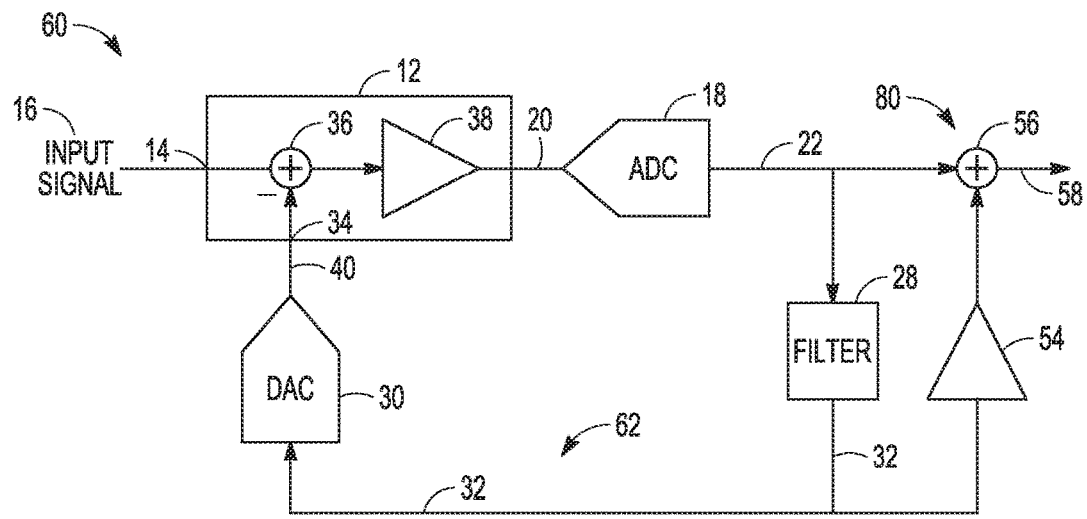
FIG. 3 depicts another example of a schematic diagram of an analog front end.

Adding a recombination path as shown in FIG. 2 can allow for an increase in the high-pass corner, and a corresponding decrease in response time, as well as a cancellation of the quantization steps. Any signal subtracted out before the analog gain in the gain circuit 12 can be added back in the digital domain via the recombination path 52, employing adder circuit 56. The success of the recombination can depend on the gain matching and linearity between the DAC/ADC path and the digital gain path. As such, it can be desirable to control the DAC 30 gain and the ADC 18 gain. These gains can be dependent upon capacitor matching, which can limit the extent to which the DAC quantization noise can be cancelled. This in turn can dictate the resolution of the SAR ADC 24. The architecture of FIG. 2 can meet the simultaneous goals of wide input range, high common-mode rejection ratio (CMRR), and quick response time. As seen in FIG. 3, however, the second ADC circuit 24 of FIG. 2, e.g. a SAR ADC, can be eliminated by using a feedback architecture, in contrast to the feed-forward architectures of FIGS. 1 and 2.

FIG. 3 depicts another example of a schematic diagram of an analog front end system 60. The system 60 in FIG. 3 can include many of the same components as the systems in FIGS. 1 and 2. For purposes of conciseness, similar components will not be described again. Rather than sampling the analog input signal 16 with the second ADC circuit 24 of FIG. 2, e.g. a SAR ADC, the system 60 of FIG. 3 can use a feedback path 62 that can eliminate the SAR ADC.

As seen in FIG. 3, the digital filter circuit 28, e.g. a low-pass filter, can receive the first digital output signal 22 of the ADC circuit 18 and provide a filtered output 32 to the DAC 30. The DAC 30 can generate an analog output signal 40 and provide the signal 40 to the second input 34 of the gain circuit 12. The adder circuit 36 can subtract the analog output signal 40 from the DAC circuit 30 from the original analog input signal 16.

In some example configurations, the DAC 30 can be a capacitive DAC, which can facilitate integration in configurations that include a capacitive gain amplifier for gain circuit 38. The DAC 30 can generate an analog output signal 40 and provide the signal 40 to the second input 34 of the gain circuit 12. The adder circuit 36 can subtract the DAC analog output signal 40 from the original analog input signal 16. It should be noted that ADC circuit 18 can be a sigma-delta ADC, a SAR ADC, or other type of ADC.

The system 60 of FIG. 3 eliminates the SAR ADC 24 of FIGS. 1 and 2, as mentioned above, and can compute the low frequency content from the output of the ADC 18 using the filter circuit 28. This configuration can reduce the power and die area consumption. However, this configuration can increase design complexity in that it is necessary to stabilize the feedback loop 62. Also, the quantization of the low-pass filter output 32 can appear as a source of quantization noise in the feedback loop. That is, a noise-shaping loop has been created.

As mentioned above and as described below with respect to FIG. 4, this document describes, among other things, an AFE system for cancelling quantization error or noise by combining an input of a filter circuit with an input of the digital-to-analog converter (DAC) circuit in the feedback loop of the AFE system. For example, by combining the input of a frequency-selective filter circuit, e.g., an input of an integrator, with the input of the DAC circuit in the feedback loop, the in-band quantization noise of the filter can be substantially eliminated, thereby improving measurement accuracy.

Figure 4:
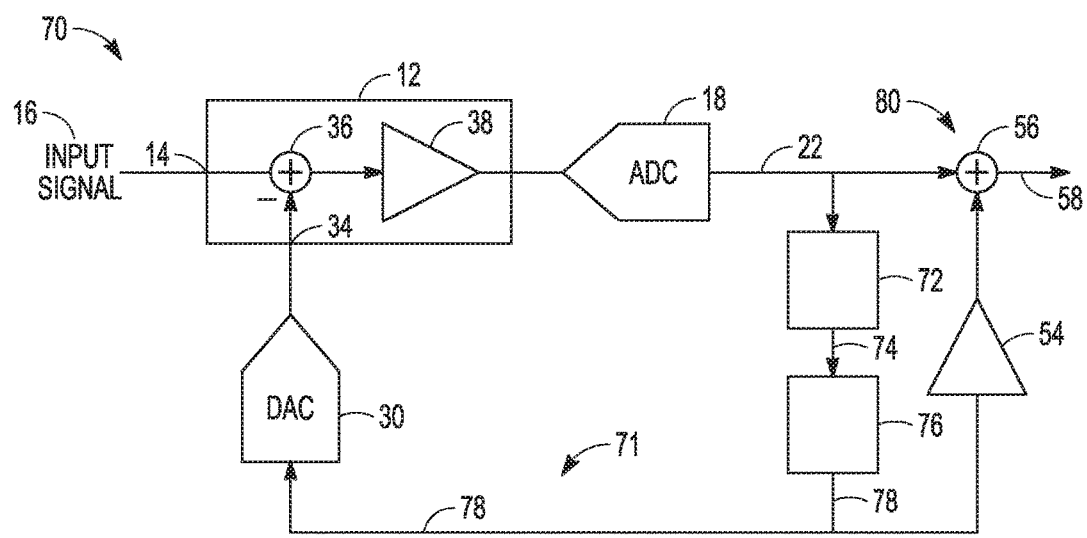
FIG. 4 depicts another example of a schematic diagram of an analog front end.

As shown in FIG. 4, the system 70 can subtract the low frequency content from the input before gain. This can be achieved by introducing a digital-to-analog converter (DAC) circuit, e.g. a capacitive DAC, as an additional input to the gain circuit 38, e.g. a CGA.

FIG. 4 depicts another example of a schematic diagram of an analog front end system 70. The system 70 in FIG. 4 can include many of the same components as the systems in FIGS. 1-3. For purposes of conciseness, similar components will not be described again. In the feedback loop 71 of FIG. 4, the filter circuit 28 in FIG. 3 has been replaced by a frequency-selective filter circuit 72 to receive the digital output signal 22 of the ADC circuit 18 and provide an output signal 74 to a quantizer circuit 76, e.g. a digital sigma-delta modulator. In some example implementations, the frequency-selective filter circuit 72 can include one or both of an integrator circuit, and a low-pass filter circuit.

As seen in FIG. 4, the quantizer circuit 76 can output a quantized signal 78 and provide the signal 78 to the DAC 30. In some examples implementations, the DAC 30 can be a noise-shaped DAC circuit, e.g. a sigma-delta DAC. In some examples, the filter circuit output signal 74 can include a first number of bits, e.g. 16 bits, and the quantized signal 78 can include a second number of bits less than the first number of bits, e.g. 7 bits.

Figure 8:
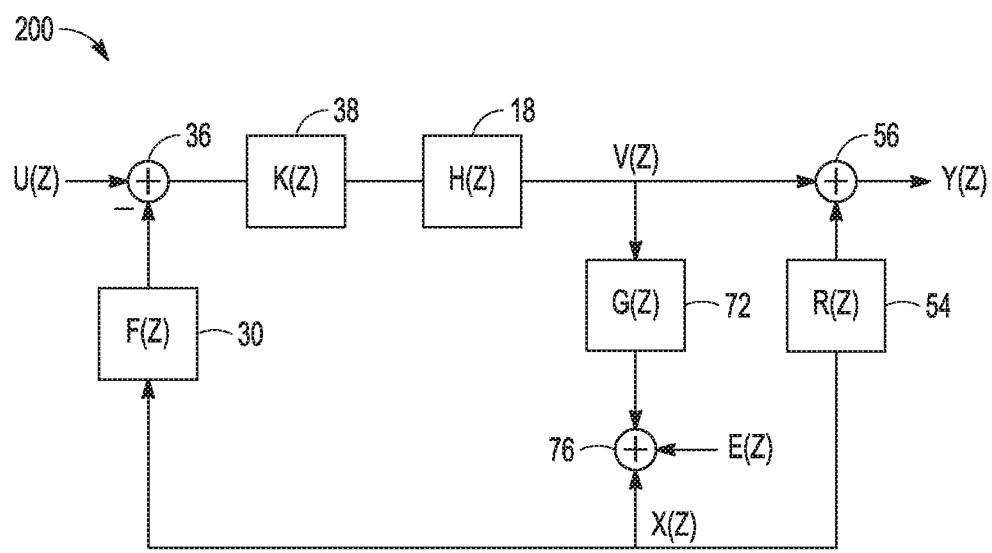
FIG. 8 depicts a block diagram of an analog front end system.

FIG. 8 depicts a block diagram of an analog front end system 200. The system 200 in FIG. 8 can include many of the same components as the systems in FIGS. 1-4. For purposes of conciseness, similar components will not be described again. Each element has an associated z-domain transfer function: gain circuit 38 has K(z), ADC circuit 18 has H(z), the frequency-selective filter circuit 72 has G(z), scaling circuit 54 has R(z), and DAC circuit 30 has F(z). The quantizer circuit 76 can be modeled as an adder with input quantization noise E(z). The adder circuit 36 can be modeled as an adder. The input signal 16 to the system is U(z). The AFE output 58 is Y(z). Equation 1 expresses the AFE output 58 in terms of the input signal 16 U(z), the quantization noise E(z), and the transfer functions for the elements. It can be seen that if Equation 2 is fulfilled, the contribution of the quantization noise is suppressed. Equation 3 then expresses the output Y(z) in terms of the input U(z). The suppression of the quantization noise depends on the extent in which R(z) matches K(z)*F(z)*H(z). The cancellation can depend on input frequency. The system can be configured so that the matching is better in the bandwidth of interest than it is outside that bandwidth. The configuration may include a trimming procedure at production test, AFE startup, periodically in the foreground, or in the background. Other trimming procedures may be known to those skilled in the art.

$$Y(z) = \frac{K(z)H(z)[1 + R(z)G(z)]}{1 + K(z)F(z)G(z)H(z)} U(z) + \frac{[R(z) - K(z)F(z)H(z)]}{1 + K(z)F(z)G(z)H(z)} E(z) \quad \text{Eq. 1}$$

$$R(z) = K(z)F(z)H(z) \quad \text{Eq. 2}$$

$$Y(z) = \frac{R(z)}{F(z)} U(z) \quad \text{Eq. 3}$$

The system 200 can further reduce the in-band quantization noise because of its noise-shaping properties, which can make the architecture more immune to gain path mismatch. The recombination error can be similar to what it was before, but the in-band noise being recombined can be less. Recombination of out-of-band noise will likely be enhanced, but this can be filtered in the decimation stages following the system 200.

In an example configuration, K(z)=8, H(z)=$z^{-3}$, G(z)=b* $(1-z^{-1})^{-1}$, F(z)=1, R(z)=$8*z^{-3}+\Delta R(z)$. These values can be substituted into Equation 1 to obtain Equation 4. Through simplification, Equation 4 yields Equation 5. It can be seen in Equation 5, that the quantization noise, E(z), is differentiated, i.e. noise-shaped. In the example, the zero-frequency quantization noise is still zero, despite a mismatch in the gain condition given by Equation 2.

$$Y(z) = \frac{8z^{-3}\left[1 + (8z^{-3} + \Delta R(z))\frac{b}{1-z^{-1}}\right]}{1 + 8\frac{b}{1-z^{-1}}z^{-3}} U(z) + \quad \text{Eq. 4}$$

$$\frac{[8z^{-3} + \Delta R(z) - 8z^{-3}]}{1 + 8\frac{b}{1-z^{-1}}z^{-3}} E(z)$$

$$Y(z) = \quad \text{Eq. 5}$$
$$8z^{-3}U(z) + \frac{8z^{-3}[\Delta R(z)b]}{1 - z^{-1} + 8bz^{-3}} U(z) + \frac{\Delta R(z)}{1 - z^{-1} + 8bz^{-3}}(1 - z^{-1})E(z)$$

Despite the reduced sensitivity to mismatch, one problem can remain: the differential non-linearity (DNL) of the DAC 30 can cause effective gain mismatches. Thus, a highly linear DAC, at least in the bandwidth of interest, can be helpful. In some example configurations, the DAC 30 can utilize dynamic element matching (DEM) techniques. In general, element rotation methods, e.g. barrel shifting, can yield lower noise than scrambling techniques. However, barrel shifting techniques can be subject to tonal behavior, so it can be desirable to pay careful attention to dithering. A practical consideration can include the number of unit elements that can be fabricated. For example, for higher resolution DACs, the number of elements in a simple element rotation scheme can become prohibitive.

Although signals in the analog domain are often implemented differentially, it should be understood that the circuits described in this disclosure are not limited to differential configurations but could be implemented in single-ended configurations.

Figure 5:
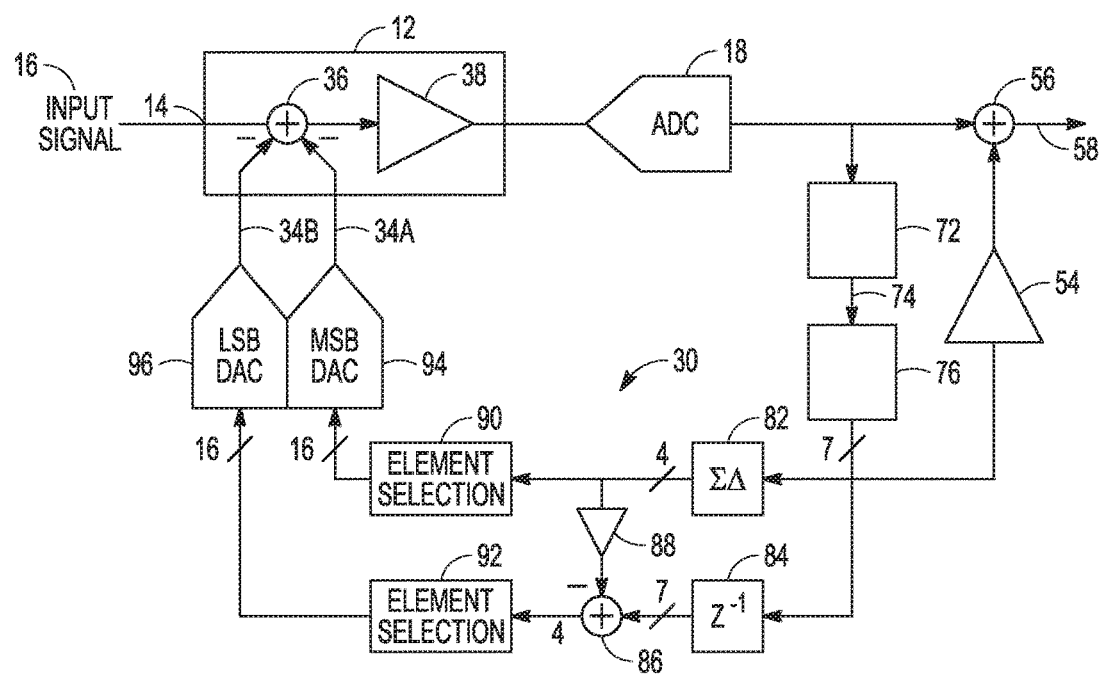
FIG. 5 depicts the example of a schematic diagram of an analog front end 70 of FIG. 4 in detail.

FIG. 5 depicts the schematic diagram of an analog front end (AFE) system 70 of FIG. 4 in detail. In particular, FIG. 5 depicts the DAC 30 of FIG. 4 in more detail. In the example implementation in FIG. 5, the DAC 30 can include a digital sigma-delta modulator circuit 82, a delay circuit 84, subtractor circuit 86, digital gain circuit 88, most significant bit (MSB) element selection circuit 90, (least significant bit (LSB) element selection circuit 92, MSB DAC circuit 94, and LSB DAC circuit 96.

As seen in FIG. 5, an M-bit output, e.g., 4 bits, digital delta-sigma modulator circuit 82 can receive an input data stream of N bits, e.g., 7 bits, from the quantizer circuit 76, where M is less than N. An output signal of the M-bit sigma-delta circuit 82 can include both the input signal as well as quantization noise from the sigma-delta circuit 82. This smaller M-bit output signal can be fed into the MSB element selection circuit 90 to perform various dynamic element matching techniques, e.g., barrel shifting, scrambling, and the like, which can perform mismatch error shaping to convert mismatch errors between DAC unit elements into high-pass shaped noise. An output signal of the MSB element selection circuit 90 can be fed into an M-bit unary MSB DAC circuit 94.

The delay circuit 84 can also receive the input data stream of N bits, e.g., 7 bits, from the quantizer circuit 76. An output signal of the delay circuit 84 can be fed into the subtractor circuit 86 along with an output of the digital scaling circuit 88, which includes the input signal as well as quantization noise from the digital sigma-delta modulator circuit 82 with gain. The input to the LSB element selection circuit 92 can be generated by the subtractor circuit 86 subtracting the input signal and quantization noise (via the output signal of the digital delta-sigma modulator circuit 82) from the input signal (via the output signal of the delay circuit 84). As such, the input to the LSB element selection circuit 92 can be the quantization noise because the input signal was canceled out by the subtractor circuit 86.

The quantization noise can be fed into the LSB element selection circuit 92 to perform various dynamic element matching techniques, barrel shifting, scrambling, and the like, which can perform mismatch error shaping. The output of the LSB element selection circuit 92 can be fed into the N−M+1 bit, e.g., 4 bit, unary LSB DAC circuit 96.

If the input signal was processed through both the M-bit MSB DAC circuit 94 as well as the LSB DAC circuit 96, gain mismatch between the MSB DAC and LSB DAC will lead to signal distortion affecting linearity and performance. The advantage of the scheme described in FIG. 5 is that the M bit MSB DAC circuit 94 carries the input signal and quantization noise while the LSB DAC circuit 96 carries only the quantization noise. At the DAC outputs 34A, 34B, the two DAC output signals can be combined together so that the quantization noise cancels and the signal passes through. Thus, any gain mismatch between the DAC circuits 94 and 96 does not cause distortion in the signal.

Figure 6:
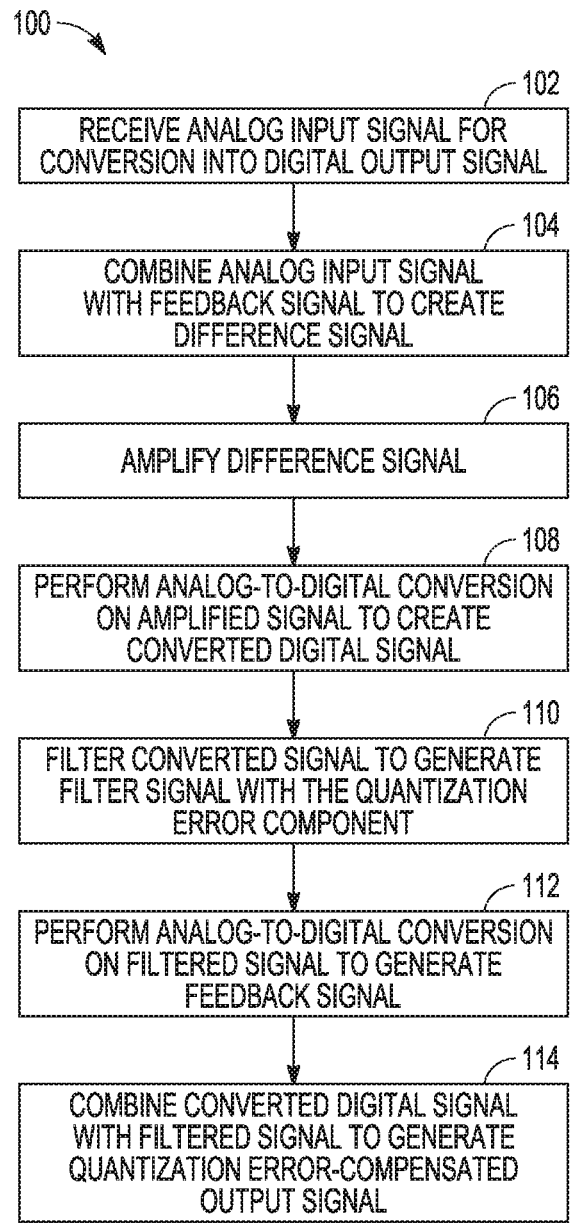
FIG. 6 is a flow diagram representing an example of a method of analog-to-digital conversion that compensates for a quantization error component of the conversion, using various techniques of this disclosure.

FIG. 6 is a flow diagram representing an example of a method 100 of analog-to-digital conversion that compensates for a quantization error component of the conversion, using various techniques of this disclosure. At block 102, the method 100 of FIG. 6 can include receiving an analog input signal for conversion into a digital output signal. For example, the gain circuit 12 of FIG. 4 can receive an analog input signal 16 for conversion into a digital output signal. At block 104, the method can include combining the analog input signal with a feedback signal to create a difference signal. For example, the adder circuit 36 of FIG. 4 can receive an analog input signal 16 at a first input and a feedback signal at a second input, and combine the two signals. At block 106, the method can include amplifying the difference signal, e.g., using gain circuit 38 of FIG. 4. At block 108, the method can include performing an analog-to-digital conversion, e.g. using a sigma-delta ADC or SAR ADC, on the amplified signal to create a converted digital signal.

At block 110, the method can include filtering the converted digital signal to generate a filtered signal with quantization error. For example, FIG. 3 includes digital filter circuit 28 for filtering the converted digital signal 22 and outputting a filter output signal 32. The digital filter output is inherently quantized. The filtering step may include integrating, low-pass filtering, or both.

At block 112, the method can include performing a digital-to-analog conversion on the filtered signal to generate the feedback signal used in block 104. For example, DAC 30 of FIG. 4 can convert the filtered signal 71 to generate the second input 34 of the gain circuit 12.

At block 114, the method can include combining the converted digital signal with the filtered signal to generate a system output in which the quantization error component is substantially reduced. For example, in FIG. 3, the filter output signal 32 is scaled by scaling circuit 54 and then added with the ADC output signal 22 via adder circuit 56 to generate the system output 58.

In some examples implementations, the method 100 of FIG. 6 can include performing an analog-to-digital conversion on the amplified signal using a sigma-delta ADC circuit to create a converted digital signal.

In some examples implementations, the method 100 of FIG. 6 can include performing an analog-to-digital conversion on the amplified signal using a successive approximation register (SAR) ADC circuit to create a converted digital.

In some example implementations, the method 100 of FIG. 6 can include additional quantization during the step of filtering the converted digital signal to generate a filtered signal with quantization error. This is exemplified in quantizer circuit 75 in FIG. 4.

The present inventors have also recognized that another problem to be solved is increasing the input dynamic range of an analog-to-digital converter system and decreasing its power consumption. The present inventors have solved this problem by integrating a digital-to-analog converter (DAC) circuit with a gain amplifier circuit, e.g. capacitive gain amplifier circuit (CGA).

As shown and explained below with respect to FIG. 7, the non-limiting example DAC circuit can include 32 DAC elements (16 MSB and 16 LSB) implemented differentially. These DAC elements can be introduced as additional inputs into the CGA. There can be a slight noise gain penalty in adding these elements. Using various techniques of this disclosure, the capacitive DAC can be integrated with the CGA.

Figure 7:
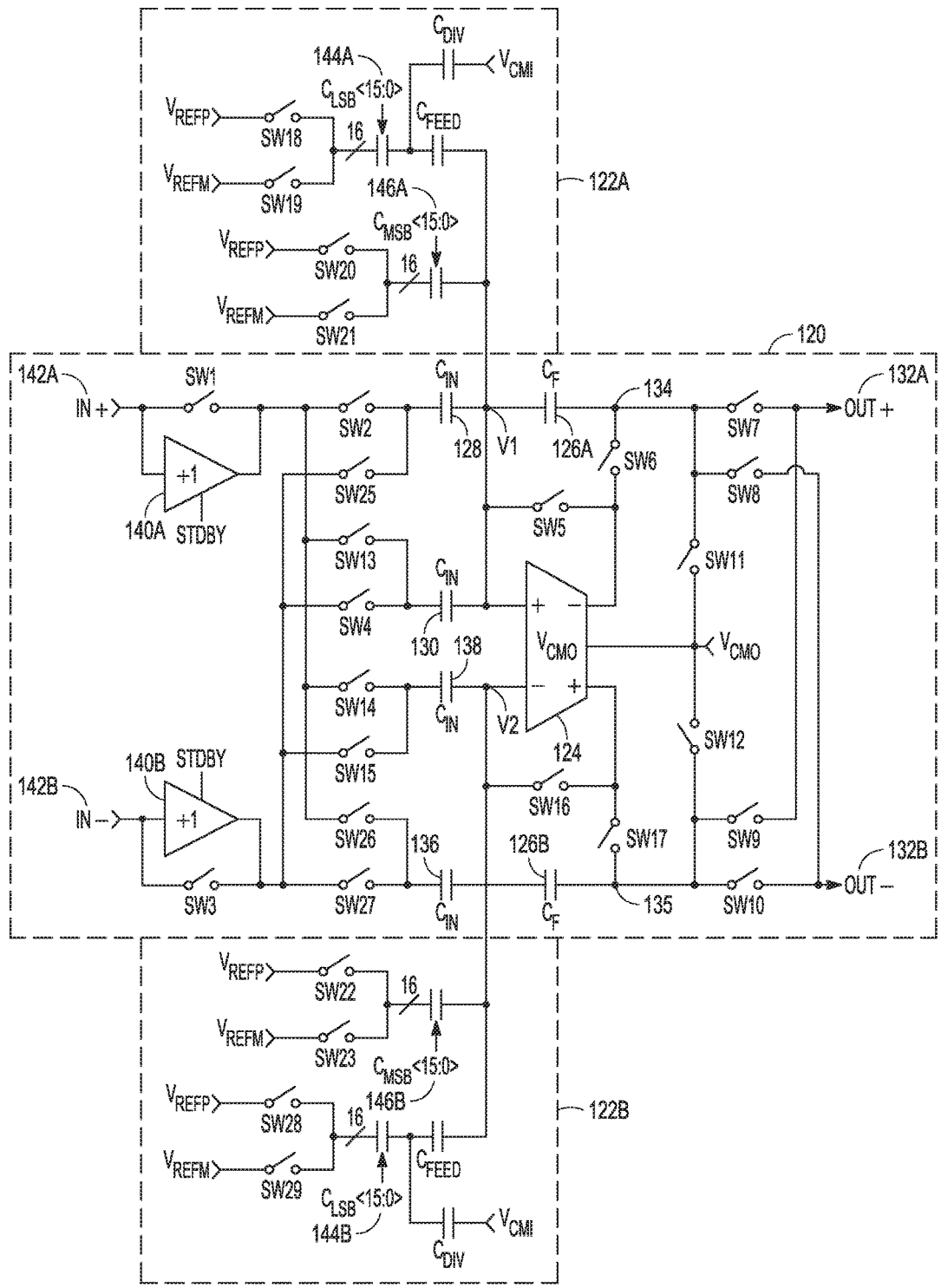
FIG. 7 depicts an example of a schematic diagram of an analog front end including a gain amplifier.

FIG. 7 depicts an example of a capacitive gain amplifier circuit 120 (CGA) and DAC circuits 122A and 122B. An example of a CGA circuit is described in commonly assigned U.S. Pat. No. 8,791,754 to Lyden et al., the entire contents of which being incorporated herein by reference. The DAC circuit 30 of FIG. 4, for example, can represent the DAC circuit 122A, 122B of FIG. 7, and the differential gain circuit 12 of FIG. 4 can represent the CGA circuit 120 of FIG. 7. As described below with respect to FIG. 7, using various techniques of this disclosure, the DAC circuit 30 and the gain circuit 12, both of FIG. 4, for example, can be integrated.

The present inventors have coupled the DAC circuits 122A, 122B with the CGA circuit 120 to cancel an input signal IN+, IN− with a feedback signal from the DAC circuits 122A, 122B such that a difference between the input signal and the feedback signal is amplified by an amplifier 124, e.g., using feedback capacitors 126A, 126B, and output as output signal OUT+ and OUT−. By using these techniques, the input dynamic range, e.g., the analog front end system 70 of FIG. 4, can be improved and a low power amplifier 124 can be used, thereby decreasing power consumption.

The DC voltage of the input nodes $V_1$ and $V_2$ of amplifier 124 can drift toward the positive and negative supply rails as they are only driven by capacitors. So the CGA 120 desirably includes an "auto-zero" mode to reset the input common mode of the amplifier periodically. In the auto-zero mode, a control circuit (not shown) of an ADC system, e.g., ADC system 70 of FIG. 4, can control the switches SW1, SW2 and SW14 to close, thereby coupling the input signal IN+ to the left-hand side input of a first positive input capacitor $C_{IN}$ 128 and input signal IN+ to the left-hand side input of a first negative input capacitor $C_{IN}$ 138.

In addition, the switches SW3, SW4 and SW27 can be closed to couple the input signal IN− to the left-hand side input of a second positive input capacitor $C_{IN}$ 130 and input signal IN− to the left-hand side input of a second negative input capacitor CIN 136. This configuration allows the left-hand side of the input capacitors 128, 130, 138 and 136 to sense the input common mode voltage. On the right-hand side of the input capacitors 128, 130, 138 and 136, switches SW5, SW16, SW11, and SW12 are closed, and switches SW6, SW7, SW8, SW9, SW17 and SW10 are open.

By way of a non-limiting example, assume that the amplifier 124 is a 1.8 Volt (V) amplifier. In the auto-zero mode with SW5 and SW16 closed, the amplifier 124 output common mode voltage, which is 0.9V in this specific example, is driven to the input terminals V1 and V2 of the amplifier 124 to set the input common mode voltage equal to the output common mode voltage. As such, the voltage at the right-hand side of the input capacitors 128, 130, 136 and 138 is at the amplifier 124 input common mode voltage (e.g., 0.9V). Referring now to the first feedback capacitor 126A, the left-hand side voltage is at the amplifier 124 input common mode voltage (e.g., 0.9V) while the right-hand side is sensed to the output common mode voltage $V_{CMO}$ directly through closed switch SW11 and SW12. As indicated above, the switches SW7-SW10 are open and thus there is no output signal present at the outputs 132A, 132B.

Now, in normal operation (or sensing mode), which can performed after the auto-zero mode is finished, the input signal IN+, IN− can be amplified using the amplifier 124. The switch SW4 can be opened and the SW13 can be closed, thereby coupling the left-hand sides of both of the positive input capacitors 128, 130 to the input signal IN+. Similarly, the switch SW14 can be opened and the SW15 can be closed, thereby coupling the left-hand sides of both the negative input capacitors 136 and 138 to the input signal IN−.

As the switch SW13 and SW15 close in the sensing mode and couple the left-hand side of the positive input capacitor 130 from IN− to IN+ and the left-hand side of the negative input capacitor 138 from IN+ to IN−, this generates a differential charge that flows through to the input terminals V1 and V2 of the amplifier 124. The switches SW5, SW16, SW11 and SW12 open and the switches SW6 and SW17 close, thereby allowing the differential charge to flow into the feedback capacitors 126A and 126B generating a differential voltage at the right-hand side of feedback capacitors 126A and 126B. The differential voltage between nodes 134 and 135 at the right-hand side of the feedback capacitors 126A and 126B is the product of the differential input voltage between inputs IN+ and IN− and the ratio of input capacitors 130 to feedback capacitor 126A.

The switches SW7-SW10 can be used to implement chopping at the output in conjunction with the input switches SW2, SW25, SW13, SW4, SW14, SW15, SW26 and SW27. The switches SW7 and SW10 can close to allow the differential voltage at nodes 134 and 135 to propagate to the output signals OUT+, OUT− at output node 132A and 132B respectively. Alternatively switches SW8 and SW9 can close to allow the differential voltage at nodes 134 and 135 to propagate to the output signals OUT−, OUT+ at output node 132B and 132A respectively.

A significant input current can be drawn as switches SW2, SW4, SW13, SW25, SW14, SW15, SW26 and SW27 are changing states to charge the left-hand side of the input capacitors 128, 130 (and the capacitors 136, 138) between the input signals IN+ and IN−. This current could disturb the sensor driving the input signal IN+, IN− and corrupt the input signal. To prevent this disruption, the CGA circuit 120 can further include buffers 140A, 140B to provide the charge to the capacitors 128, 130 and the capacitors 136, 138 periodically while switches SW1 and SW3 are open. After charging the capacitors 128, 130 and the capacitors 136, 138, a control circuit can place the buffers 140A, 140B in a standby mode and bypass the buffers 140A, 140B by closing switches SW1, SW3 before the ADC system after the CGA begins sampling. As such, any noise associated with the buffers 140A, 140B is not added to the overall system noise.

Assume that the output range between the output nodes 136A, 136B is a voltage Vx and that the gain of the amplifier circuit 124 is 8, then the input range between the input nodes 142A, 142B is Vx/8. Ordinarily, this means that applying an input signal having a voltage of Vx/2 can cause the output nodes to over-range. So, for a fixed output range, any increase in amplifier gain can result in a smaller input dynamic range.

The present inventors have recognized that, by integrating a DAC circuit 122A, 122B with the CGA circuit 120, the input signal can be canceled to a first order so that the difference is gained up. By way of a non-limiting specific example, assume that the output voltage has a differential range of 5V and the amplifier circuit 124 has a gain of 8. If the differential input voltage is 2V, then the output would over-range (2V*8). However, using the techniques of this disclosure, a feedback signal can cancel 1.9V (for example) of the 2V differential input voltage. Applying a gain of 8 to the 0.1V signal, the output voltage is 0.8V. Thus, the integration of the DAC circuit 122A, 122B can increase the input dynamic range of the CGA circuit 120. In addition, because the output voltage range can be reduced, a low power amplifier 124 can be used.

Referring now to the DAC circuit 122A, the capacitor groups $C_{LSB}$ 144A and $C_{MSB}$ 146A of the DAC circuit 122A can be reset during the auto-zero mode described above. To reset the capacitor groups $C_{LSB}$ 144A and $C_{MSB}$ 146A, the control circuit can couple half of the capacitors in each of the groups $C_{LSB}$ 144A and $C_{MSB}$ 146A to a positive reference voltage $V_{REFP}$ and the other half in each of the groups $C_{LSB}$ 144A and $C_{MSB}$ 146A to a negative reference voltage $V_{REFM}$. This is similar to how the input capacitors 128, 130 (and capacitors 136, 138) of the CGA circuit 120 were reset, where half of input capacitors were coupled to IN+ and half were coupled to VIN−. It should be understood that the switches SW18-SW21, SW22, SW23, SW28, and SW29 can represent sets of switches, e.g., 16 switches <15:0>, to couple to respective capacitors 144A, 144B, 146A, and 146B.

However, there can be mismatches in the capacitors of the capacitor groups $C_{LSB}$ and $C_{MSB}$. As such, even when half of the capacitors in the capacitor group $C_{MSB}$, e.g., 8 capacitors, are coupled to the positive reference voltage $V_{REFP}$ and the other half of the capacitors in the capacitor group $C_{MSB}$, e.g., 8 capacitors, are coupled to the negative reference voltage $V_{REFM}$, there can be auto-zero errors due to mismatch errors between the capacitors. Similar auto-zero errors can occur with the capacitor group $C_{LSB}$. Dynamic element matching (DEM) techniques, e.g., barrel shifting and the like, can be used to noise shape any capacitor mismatches in the auto-zero mode. The capacitor groups $C_{LSB}$ 144B and $C_{MSB}$ 146B of the DAC circuit 122B can be reset using similar techniques.

After the auto-zero mode and in normal mode (sensing mode), a feedback signal from the ADC system can control the MSB switches SW20 to couple one or more capacitors of the MSB capacitor group $C_{MSB}$ 146A to a positive reference voltage $V_{REFP}$ and can control the MSB switches SW21 to couple one or more capacitors of the MSB capacitor group $C_{MSB}$ 146A to a negative reference voltage $V_{REFM}$. In a specific non-limiting example for purposes of description, the feedback signal can control the MSB switches SW20 to couple 8 capacitors of the MSB capacitor group $C_{MSB}$ 146A to a positive reference voltage $V_{REFP}$ and can control the MSB switches SW21 to couple 8 capacitors of the MSB capacitor group $C_{MSB}$ 146A to a negative reference voltage $V_{REFM}$.

Similarly, in the DAC 122B, the inverse of the feedback signal can control the MSB switches SW22 to couple one or more capacitors of the MSB capacitor group $C_{MSB}$ 146B to a positive reference voltage $V_{REFP}$ and can control the MSB switches SW23 to couple one or more capacitors of the MSB capacitor group $C_{MSB}$ 146B to a negative reference voltage $V_{REFM}$. Continuing the specific non-limiting example above, the feedback signal can control the MSB switch SW22 to couple 8 capacitors of the MSB capacitor group $C_{MSB}$ 146B to a positive reference voltage $V_{REFP}$ and can control the MSB switch SW23 to couple 8 capacitors of the MSB capacitor group $C_{MSB}$ 146B to a negative reference voltage $V_{REFM}$. This differential connection of the DAC circuits 122A, 122B results in a differential charge at nodes $V_1$ and $V_2$ at input terminals of the amplifier 124. This differential charge can cancel most of the input differential charge at the input capacitors 128, 130, 136, 138. As a result, the difference between the differential charge from the DAC circuits 122A and 122B and the input differential charge from the input capacitors 128, 130, 136 and 138 is placed on the feedback capacitors 126A, 126B.

Integrating the DAC circuits 122A, 122B with the CGA. 120, as described above, can provide several advantages. First, the difference signal, and not the full input signal, can be amplified by the amplifier 124. As indicated above, this can increase the input dynamic range of the CGA circuit 120. Second, the output voltage range can be reduced, thus allowing a low power amplifier 124 to be used.

In a specific non-limiting example of an application, the circuit of FIG. 7 can be used in an analog front end circuit in an ECG front end. In such an application, the ECG input signal can be, for example, a 10 mV signal on a 1V offset. The techniques of FIG. 7 can allow the 1V offset to be canceled using the DAC circuit 122A, 122B, permitting the 10 mV ECG signal to be fed through and amplified by the amplifier 120.

As mentioned above, in some example implementations, various techniques of this disclosure can be used for wireless patient monitoring. In some examples, this disclosure describes a measurement channel capable of providing diagnostic quality ECG measurements such as for battery-powered wireless patient monitoring. Each channel can provide 21-bit output at either 300 SPS or 600 SPS. The noise per channel is approximately 1.5 $\mu N_{rms}$. For robust use in the face of severe interference, the input dynamic range is greater than ±1 V, with an overload recovery time of less than 16.6 ms. Input bias currents can be maintained below 250 pA such as not to interfere with other monitoring functions. The architecture discussed suits itself to general analog-to-digital conversion.

As an introduction, electrocardiogram (ECG) measurement contends with a host of interference sources. Electrode offset potentials, electrosurgery, electrostatic discharge, triboelectric effects, 50/60 Hz line noise, pacemaker pulses and motion artifacts present spurious signals that should be rejected during normal operation. Additionally, de lead off detection, ac lead quality measurement, and thoracic impedance measurements can operate concurrently with ECG, injecting their own disturbances that should be rejected. ECG measurement channels should also not interfere with other measurements. In most cases, interference should not result in artifacts on the output cardiogram. However, some events can saturate an ECG front end (e.g. large amplitude pacemaker pulses). In these cases, the restoration time can be important for maintaining clinically acceptable output. The analog front end (AFE) presented can provide a ±1 V input differential range and a ±1.25 V input common-mode range. The recovery time after an overload event can be less than 1 line cycle (16.6 ms worst case); this can actually be limited by the analog front end decimation filtering and not by the AFE. The combination of a wide input range and fast response time can result in robust performance in the face of interference.

Design of a practical ECG front end can involve careful accounting of the input headroom. The actual ECG signal does not typically exceed 50 mV. The most significant contributor to the headroom budget can be the electrode offset potential. For "wet" electrodes this is typically less than ±300 mV, but for "dry" electrodes this can be as large as ±700 mV. Another large signal that can be present differentially is the 50/60 Hz line noise which typically has an amplitude in the range of tens of millivolts. This signal will be converted and should then eliminated in digital post-processing. Motion artifacts can induce spurious signals with tens of millivolts of amplitude. These can have a range of frequency content which can make them difficult to remove via filleting. As such they may be just passed along to be interpreted by the clinician. There are other signals even more difficult to quantify.

In some patients, a pacemaker may add a dynamic signal of amplitude ranging from 2 mV (or less) to 700 mV (max). These are short pulses with a duration of 100 µs to 2.0 ms. ECG system manufacturers may desire an extension of the valid pulse amplitude and duration range to accommodate the variety of pacemakers on the market. From the point of view of an ECG front end, these pulses appear to be impulses. However, they may still saturate the signal chain due to the large amplitude. Similar to pacemaker pulses, electrostatic discharge (ESD) and triboelectric pulses from infusion pumps can cause impulsive noise. The front end is desired to recover quickly in cases in which impulses cause a saturation event. For effective blanking of pacemaker pulses without loss of clinical information, the recovery time constant should be short relative to the pulse rate. A recovery time of 15 ms can be chosen in an example of the present implementation.

Possibly the most difficult interferer to contend with is electrosurgery. Electrosurgery involves high voltage discharges from a resonant tank circuit which results in aperiodic arcing. An ECG system can clamp and filter the electrode inputs, such as to inhibit or prevent front end damage. Much of the signal can present as a common-mode voltage, yet the large voltages involved can easily translate circuit asymmetries and non-linearities into differential voltage. Estimating the signal level is complicated in that it depends on a variety of circumstances: the electrosurgery stimulus, the location of electrodes, the tissue that is being cut, the rate of cutting, parasitic circuit paths. Some amount of common-mode signal can be suppressed by the reference electrode drive (RED)/right leg drive (RLD) feedback loop. The residual of the common-mode and all of the differential voltage presents to the analog front end. The proposed front end is configured to continue to give clinical quality output during high-voltage/high-power surgery. In the most extreme cases, the input clamping structures may cause signal distortion before the front end saturates. If the front end does eventually saturate, it is configured to recover quickly. In general, the larger the differential and common-mode range of the front end, the better the electrosurgery immunity will be. This configuration has budgeted ±100 mV of differential signal (at the front end input) and ±1.25 V of common-mode range.

The common-mode component of 50/60 Hz noise can be quite large but can be suppressed with a RED/RLD feedback loop. The residual common-mode signal should be handled by the common-mode range of the ECG front end. Determining the magnitude of this effect can be complicated as it can depend on parasitic paths in the ECG system. One approach that can be used for configuration is to use past experience for the level of interference. This can be supplemented with simulations in which estimates of the parasitic coupling paths are made. As it may be required that common-mode line rejection be measured without a post-processing filter in place, it is desirable that the front have a reasonably high common-mode rejection ratio at line frequencies. The combination of the RED loop and high channel CMRR may be sufficient to mitigate the common-mode line noise interference for headroom considerations. It can imply a constraint that the front end CMRR be on the order of 80 dB.

In addition to external sources of interference, an ECG front end may contend with other measurement stimuli. In particular, the system should budget headroom for de lead off detection. Typical good electrode connection impedances can be approximated by 51 kΩ in parallel with 47 nF. Actual electrodes can present lower impedance than this. However when connections are first made and then after some period of time the impedance can degrade considerably. Although standards suggest an impedance of 510 kΩ and 4.7 nF, this may be optimistic. The resistive component can rise to as much as 30 MΩ before being replaced in the clinical setting—the thermal noise can become quite objectionable. If dc lead off detection currents are set around 10 nA, as much as 0.3 V of input headroom can be consumed. If this occurs on both electrodes of a differential measurement, this amounts to 0.6 V of headroom. It may not be realistic to assume both maximum electrode offset and maximum de lead off voltage, so a compromise level of differential input range can be settled upon.

Two minor sources of additional headroom consumption are thoracic impedance measurement and ac lead quality measurement. Thoracic impedance measurements can be done to monitor respiration, especially in a post-operative context and for newborns. In order to avoid consuming measurement headroom with the electrode impedance, the stimulus frequency is typically well above 10 kHz. The voltage amplitude of the stimulus is typically over 1 V. This sees a voltage divider between the current setting resistor and the body impedance. This is then filtered by the Electrosurgery Interference Suppression (ESIS) filter. Referred to the input of the ECG front end, the amplitude will see a reduction by 30 dB. This puts the amplitude around 50 mV, Ac lead quality measurement can be done at a frequency just outside the ECG band. If the drive source can be maintained in the tens of nanoamps, then the worst case amplitude will be no more than 100 mV. Thus, thoracic impedance measurements and ac lead quality measurements can detract an addition ±150 mV of input differential headroom.

Consideration of the major interference sources can lead to the conclusion that at least ±1 V of input differential headroom is necessary for robust ECG performance. TABLE I summarizes the interference sources and their magnitudes:

TABLE I

SUMMARY OF ECG HEADROOM

| Interference Source | Worst Case Magnitude | Budgeted Magnitude |
|---|---|---|
| ECG Signal | ±50 mV | ±50 mV |
| Electrode Offset | ±700 mV | ±300 mV |
| Differential 50/60 Hz Line Noise | ±50 mV | ±50 mV |
| Motion Artifacts | Tens of mV | ±50 mV |
| Pacemaker Pulses | ±700 mV | ±200 mV |
| Electrosurgery | ??? | ±100 mV |
| Dc Lead Off Measurement | ±600 mV | ±100 mV |
| Thoracic Impedance Measurement | ±50 mV | ±50 mV |
| Ac Lead Quality Measurement | ±100 mV | ±100 mV |
| Total | ±2300 mV | ±1000 mV |

It is unlikely that all the sources will be at the worst case simultaneously. As such a rough budget can be drawn up as in the third column of the table. The actual numbers will vary depending on the patient, but a ±1 V input differential range should suffice to cover every situation; it is always possible for the clinician to replace the contacts if they have excessive offset and/or impedance while other major interferers are present. Summarizing, the front end should have a differential input range of ±1 V, a CMRR of 80 dB, and a recovery time of approximately 15 ms.

As discussed above, the ECG channel should have an input differential range of at least ±1 V and a common-mode range of ±1.25 V. Such a large swing can require a supply voltage of at least 3.5 V; the closest available supply can be 5.0 V. The current draw from the 5.0 V supply should be minimized. Additionally, to provide adequate common-mode rejection, the front end should have a CMRR of greater than 80 dB. For cases when the front end saturates, it should recover in less than 15 ms.

Additionally, the ECG standards specify a maximum 30 $\mu V_{pp}$ noise over a 10 s period for nine out of ten trials. Statistical simulations using Gaussian white noise indicates a relationship that the peak-to-peak noise is 8.3 times the standard deviation of the rms noise. This indicates the rms noise should be less than 3.6 $\mu V_{rms}$. Allowing for other sources of noise in the system (e.g. electrosurgery filters, electrode resistance, de lead off stimulus current noise, etc.), a channel noise target of 1.5 $\mu V_{rms}$ was chosen. This provides an ample margin across operating conditions versus the standards.

The proposed channel architecture of FIGS. 4 and 5 adheres to a general principle that sampling should be done after some amount of gain is taken. However even with a power supply voltage of 5 V, given a ±1 V input range, not even a de gain of 2.5 gain can be obtained. This can necessitate either ac coupling or a scheme to subtract out some portion of the input before taking the gain. Ac coupling for ECG applications has the drawback that the recovery time after overload events can be prohibitively long; recovery often introduces significant artifacts. With this in mind, a subtractive scheme can be preferable.

To minimize the noise, a capacitive gain amplifier (CGA) can be chosen. This can avoid the thermal noise associated with gain setting resistors. Additionally, stages that introduce chopping before the input capacitors can be used to yield a higher CMRR. Biasing of CGA stages can be challenging. The biasing scheme described in this document can work well in discrete-time systems. In addition to the CGA, a circuit to subtract the low frequency content of the differential input can be implemented, as described above.

VARIOUS NOTES

Each of the non-limiting aspects or examples described herein may stand on its own, or may be combined in various permutations or combinations with one or more of the other examples.

The above detailed description includes references to the accompanying drawings, which form a part of the detailed description. The drawings show, by way of illustration, specific embodiments in which the invention may be practiced. These embodiments are also referred to herein as "aspects" or "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g. compact discs and digital video discs), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 CFR § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

What is claimed is:

1. An analog front end (AFE) system for compensating quantization error, the AFE system comprising:
   a gain circuit including a first input configured to receive an input signal, a second input configured to receive a feedback signal using a feedback path, and an output configured to provide an amplified version of the difference between the input signal and the feedback signal;
   an analog-to-digital converter (ADC) configured to receive a gain circuit output signal and output a digital output signal;
   a digital frequency-selective filter circuit configured to receive the ADC digital output signal and output a quantized filter circuit output signal;
   a digital-to-analog converter (DAC) circuit, the DAC circuit configured to receive the filter output signal and output the feedback signal to the second input of the gain circuit; and
   an AFE system output circuit configured to combine the ADC output signal and the filter circuit output signal, and output a quantization error-compensated AFE output signal.

2. The AFE system of claim 1, wherein the gain circuit output is configured to be periodically sampled to substantially reject any sampling noise contribution of the gain circuit.

3. The AFE system of claim 1, wherein the gain circuit comprises capacitive gain-setting elements.

4. The AFE system of claim 1, wherein the digital frequency-selective filter includes a quantizer circuit to output the quantized filter circuit output signal.

5. The ATE system of claim 4, wherein the quantizer circuit includes a sigma-delta circuit.

6. The AFE system of claim 4, wherein the quantizer circuit receives a filtered signal having a first number of bits, and wherein the quantized filter circuit output signal has a second number of bits less than the first number of bits.

7. The AFE system of claim 1, wherein the ADC includes a sigma-delta ADC circuit.

8. The AFE system of claim 1, wherein the ADC includes a successive approximation register (SAR) ADC circuit.

9. The AFE, system of claim 1, DAC circuit is configured to perform dynamic element matching.

10. The AFE system of claim 1, wherein the gain circuit includes a capacitive gain amplifier (CGA) circuit.

11. The AFE system of claim 1, wherein the digital frequency-selective filter circuit includes an integrator.

12. The AFE system of claim 1, where the digital frequency-selective filter circuit includes a low-pass filter circuit.

13. A method of analog-to-digital conversion that compensates for a quantization error component of the conversion, the method comprising:
   receiving an analog input signal for conversion into a digital output signal;

combining the analog input signal with a feedback signal to create difference signal;

amplifying the difference signal;

performing an analog-to-digital conversion on the amplified signal to create a converted digital signal;

filtering the converted digital signal to generate a filtered signal with quantization error;

performing a digital-to-analog conversion on the filtered signal to generate the feedback signal; and combining the converted digital signal with the filtered signal to generate a system output in which the quantization error component is substantially reduced.

14. The method of claim 13, wherein performing an analog-to-digital conversion on the amplified signal includes:

performing an analog-to-digital conversion using a sigma-delta converter on the amplified signal to create a converted digital signal.

15. The method of claim 13, wherein performing an analog-to-digital conversion on the amplified signal includes:

performing an analog-to-digital conversion using a successive-approximation-register (SA) converter on the amplified signal to create a converted digital signal.

16. The method of claim 13, wherein filtering the converted digital signal to generate a filtered signal with quantization error includes:

filtering the converted digital signal and then quantizing the result.

17. The method of claim 16, wherein quantizing the result includes:

quantizing the result using a noise-shaping quantizer circuit.

18. The method of claim 13, filtering the converted digital signal to generate a filtered signal with quantization error includes:

using a frequency-selective filter including an integrator.

19. The method of claim 13, filtering the converted digital signal to generate a filtered signal with quantization error includes:

using a frequency-selective filter including a low-pass filter.

20. An electrocardiogram (ECG) measurement circuit comprising:

an analog front end (AFE) system for compensating quantization error, the AFE system including:

a gain circuit including a first input configured to receive an input signal and a second input configured to receive a feedback signal using a feedback path;

an ADC circuit configured to receive a gain circuit output signal and output an ADC circuit output signal;

a frequency-selective filter circuit configured to receive the ADC circuit output signal and output a filter circuit output signal;

a quantizer circuit, the quantizer circuit configured to receive the filter circuit output signal and output a quantized signal;

a digital-to-analog converter (DAC) circuit, the DAC circuit configured to receive the quantized signal and output the feedback signal to the second input of the gain circuit; and an AFE system output circuit configured to combine the ADC circuit output signal and the quantized signal and output a quantization error-compensated AFE output signal.

21. The ECG measurement circuit of claim 20, wherein the gain circuit output is configured to be periodically sampled to substantially reject any sampling noise contribution of the gain circuit.

22. The ECG measurement circuit of claim 20, wherein the digital frequency-selective filter includes a quantizer circuit to output the quantized filter circuit output signal.

23. The ECG measurement circuit of claim 22, wherein the quantizer circuit includes a sigma-delta circuit.

24. The ECG measurement circuit of claim 22, wherein the quantizer circuit receives a filtered signal having a first number of bits, and wherein the quantized filter circuit output signal has a second number of bits less than the first number of bits.

* * * * *

UNITED STATES PATENT AND TRADEMARK OFFICE
CERTIFICATE OF CORRECTION

| | | |
|---|---|---|
| PATENT NO. | : 10,327,659 B2 | Page 1 of 1 |
| APPLICATION NO. | : 15/621621 | |
| DATED | : June 25, 2019 | |
| INVENTOR(S) | : Kalb et al. | |

It is certified that error appears in the above-identified patent and that said Letters Patent is hereby corrected as shown below:

On the Title Page

On page 2, in Column 2, under "Other Publications", Line 13, delete "2uW 100 n V/rtHz" and insert --2 µW 100 nV/rtHz-- therefor On page 2, in Column 2, under "Other Publications", Line 14, after "for", insert --Chronic--

On page 2, in Column 2, under "Other Publications", Line 17, delete "mm2, 5uW," and insert --$mm^2$, 5 µW,-- therefor In the Claims In Column 18, Line 44, in Claim 5, delete "ATE" and insert --AFE-- therefor In Column 18, Line 54, in Claim 9, delete "AFE," and insert --AFE-- therefor In Column 18, Line 54, in Claim 9, before "DAC", insert --wherein the--

In Column 19, Line 23, in Claim 15, delete "(SA)" and insert --(SAR)-- therefor

<div style="text-align: right;">
Signed and Sealed this  
Twenty-first Day of April, 2020

Andrei Iancu  
*Director of the United States Patent and Trademark Office*
</div>